United States Patent
Gadberry et al.

(10) Patent No.: US 7,578,827 B2
(45) Date of Patent: Aug. 25, 2009

(54) SUTURE CLIP WITH STOP RIBS AND METHOD FOR MAKING SAME

(75) Inventors: Donald L. Gadberry, San Juan Capistrano, CA (US); Gary M. Johnson, Mission Viejo, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 641 days.

(21) Appl. No.: 10/817,259

(22) Filed: Apr. 2, 2004

(65) Prior Publication Data

US 2005/0222590 A1  Oct. 6, 2005

(51) Int. Cl.
*A61B 17/08* (2006.01)
(52) U.S. Cl. .................... 606/151; 606/157
(58) Field of Classification Search ......... 606/151–155, 606/157, 120, 142, 143
See application file for complete search history.

(56) References Cited

U.S. PATENT DOCUMENTS

| | | | | |
|---|---|---|---|---|
| 3,182,373 | A * | 5/1965 | Strand | 251/7 |
| 3,509,882 | A * | 5/1970 | Blake | 606/142 |
| 3,510,923 | A * | 5/1970 | Blake | 606/158 |
| 4,390,019 | A * | 6/1983 | LeVeen et al. | 606/158 |
| 4,681,109 | A * | 7/1987 | Arroyo | 606/158 |
| 4,817,604 | A * | 4/1989 | Smith, III | 606/151 |
| 4,931,058 | A * | 6/1990 | Cooper | 606/158 |
| 4,932,955 | A * | 6/1990 | Merz et al. | 606/158 |
| 4,976,721 | A * | 12/1990 | Blasnik et al. | 606/157 |
| 5,335,398 | A * | 8/1994 | Schottker et al. | 24/528 |
| 5,653,720 | A * | 8/1997 | Johnson et al. | 606/151 |
| 5,984,934 | A * | 11/1999 | Ashby et al. | 606/151 |
| 6,267,773 | B1 * | 7/2001 | Gadberry et al. | 606/151 |
| 6,802,848 | B2 * | 10/2004 | Anderson et al. | 606/157 |
| 6,821,284 | B2 * | 11/2004 | Sturtz et al. | 606/151 |
| 7,144,402 | B2 * | 12/2006 | Kuester, III | 606/158 |

OTHER PUBLICATIONS

International Search Report and Written Opinion of the International Searching Authority for PCT application PCT/US2005/009780, mailed Aug. 16, 2005, Applied Medical Resources Corporation.
Co-Pending U.S. Appl. No. 11/954,457, filed Dec. 12, 2007; Title: Surgical Clip.
Co-Pending U.S. Appl. No. 10/935,967, filed Sep. 8, 2004; Title: Surgical Clip.
Co-Pending U.S. Appl. No. 10/612,631, filed Jul. 2, 2003; Title: Interlocking Suture Clinch.
Co-Pending U.S. Appl. No. 10/533,398, filed Apr. 30, 2005; Title: Surgical Staple-Clip and Applier.

(Continued)

*Primary Examiner*—Darwin P Erezo
(74) *Attorney, Agent, or Firm*—John F. Heal; David G. Majdali; Patrick Y. Ikehara

(57) ABSTRACT

A suture clip with stop ribs and method for making same is provided. The clip includes a housing having an outer surface, and a pair of jaws extending longitudinally from the housing in an opposing relationship to each other. A resilient pad is carried by one of the jaws and defines with the outer surface of the housing a shutoff cavity. At least one rib extends longitudinally of the housing and across the cavity to inhibit any undesirable passage of the suture into the cavity.

8 Claims, 13 Drawing Sheets

OTHER PUBLICATIONS

Co-Pending U.S. Appl. No. 11/280,098, filed Nov. 15, 2005; Title: Partial Occlusion Surgical Guide Clip.
Co-Pending U.S. Appl. No. 10/702,871, filed Nov. 5, 2003; Title: Suture Securing Device and Method.
Co-Pending U.S. Appl. No. 10/986,993, filed Nov. 12, 2004; Title: Overmolded Grasper Jaw.
Co-Pending U.S. Appl. No. 10/543,800, filed Jul. 29, 2005; Title: Spring Clip and Method for Assembling Same.

* cited by examiner

SUTURE CLIP WITH STOP RIBS AND METHOD FOR MAKING SAME

BACKGROUND OF THE INVENTION

1. Field of the Invention

This invention relates generally to clips and clamps and, more specifically, to surgical clips adapted for use in retaining sutures.

2. Discussion of Related Art

Surgical clips are commonly formed with first and second telescoping members each attached to any elongate jaw of the clip. The telescoping members form a housing for a compression spring which biases the opposing jaws to a closed state. The jaws are commonly formed of hard plastic that are typically covered with soft elastomeric pads for atraumatically engaging and occulting blood vessels and other surgical elements such as sutures.

With the hard plastic jaws and soft pads, these clips are excellent candidates for a two-shot molding process where the hard plastic jaw is formed in a mold, and the soft pads are formed in a second mold. In this process, the harder material is molded and permitted to solidify. It then forms a part of the second mold which is used to form the soft pads directly on the hard plastic jaw. The second mold typically includes mold shutoffs which modify the first mold and facilitate formation of the second mold with the hard jaws.

In the past, use of these mold shutoffs has produced a void or slot at the proximal interface between the soft pad and the hard jaw. Sutures and other objects intended to be held by the clips have tended to fall into these shutoff voids severely complicating the clipping process.

SUMMARY OF THE INVENTION

In accordance with the present invention, ribs are formed in the vicinity of the shutoff void and form part of the second mold. These ribs extend through the shutoff void at a height sufficient to render it impossible for a suture to fall into the void. The mold shutoff used to define the second mold is seated on these ribs when the second mold is formed. In this manner, ribs can be formed on both of the opposing jaws of the clip preferably offset so that they do not contact each other when the jaws are closed.

In this manner, the highly advantage two-shot mold process can be accommodated even using mold shutoffs, without producing a significant shutoff void. As a result, a surgical clip can be formed with the highly advantages two-shot mold process and adapted for use with smaller objects such as sutures.

In accordance with one aspect of the invention, a surgical clip is adapted for use in holding a suture. The clip includes a housing having an outer surface, and a pair of jaws extending longitudinally from the housing in an opposing relationship to each other.

A resilient pad is carried by one of the jaws and defines with the outer surface of the housing a shutoff cavity. At least one rib extends longitudinally of the housing and across the cavity to inhibit any undesirable passage of the suture into the cavity.

In another aspect, the surgical clip includes a housing with an inner member and an outer member having a telescoping relationship. A first jaw extends from the inner member outwardly of the housing and has a first inner surface. A second jaw extends from the outer member outwardly of the housing and has a second inner surface. The jaws are moveable between an open position and a closed position in an opposing relationship, with the first surface of the first jaw facing the second surface of the second jaw. At least one first rib extends from the first surface of the first jaw toward the second surface of the second jaw, and at least one second rib extends from the second surface of the second jaw toward the first surface of the first jaw. These ribs have a non-interfering relationship when the jaws are in the closed position.

In another aspect, the invention includes a method for making a surgical clip having a housing formed of telescoping members each with an outer surface. First and second opposing jaws are associated with the telescoping members. One of the telescoping members is molded with its associated jaw in a first mold. Following this first molding step a pad is molded onto the first jaw in the first mold. During the first molding step at least one rib is molded onto the first jaw to extend from the outer surface of the associated member along the first jaw. During the second molding step, a mold shutoff is seated against the first jaw and the at least one rib to form a mold cavity for the pad.

These and other features and advantages of the invention will become more apparent with a description of preferred embodiments and reference to the associated drawings.

DESCRIPTION OF PREFERRED EMBODIMENTS AND BEST MODE OF THE INVENTION

Figure 1:
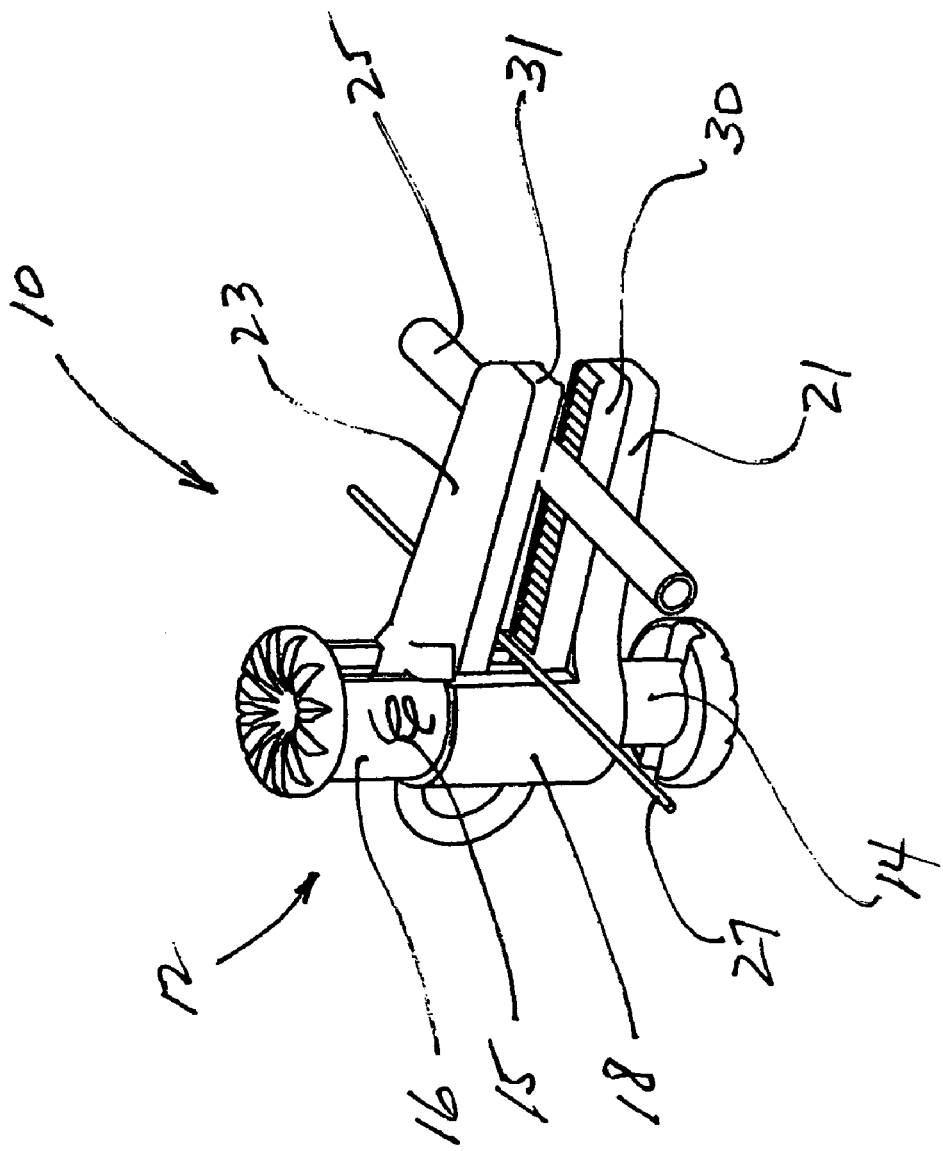
FIG. 1 is a perspective view of a surgical clip in accordance with the prior art.

A surgical clip of the prior art is illustrated in FIG. 1 and designated by the reference numeral 10. The clip 10 includes telescoping members 12 and 14 which form a housing for a compression spring 15. In order to facilitate assembly, the first telescoping member 12 will typically be formed as two components 16 and 18, which are snap-fit together. An upper jaw 21 is integral with the telescoping member 14 while a lower jaw 23 is integral with the telescoping member 12. As these members 12 and 14 are squeezed together against the bias of the spring 15, the jaws 21 and 23 are moved to an open state. When the members 12 and 14 are released, the spring 15 biases the jaws 21 and 23 to a closed state as illustrated in FIG. 1. In this closed state, the opposing jaws 21 and 23 are adapted to engage various objects associated with the surgery.

These objects may include items of tissue, such as a blood vessel, or other objects associated with the surgery, such as a suture 27. Particularly in the case of a vessel 25, it is desirable that the jaws 21 and 23 be provided with soft or elastomeric pads 30 and 31, respectively, which provide for atraumatic engagement and perhaps occlusion of the vessel 25.

Figure 2:
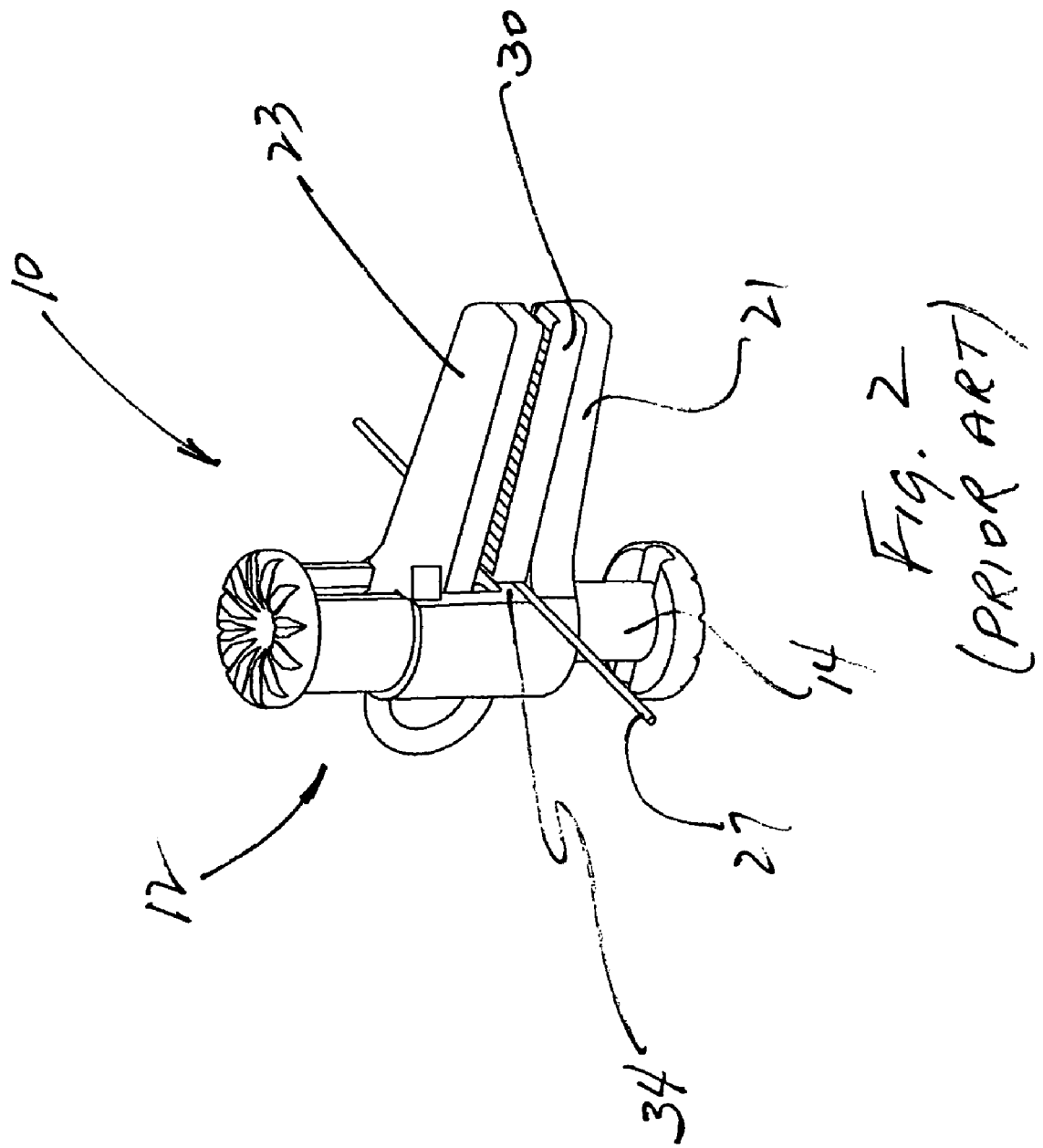
FIG. 2 is a perspective view of the clip of FIG. 1 and illustrates a problem with the two-step molding process of the prior art.

In a method of manufacture of the invention, the soft pad 30 can be molded directly onto the hard jaw 21 in a two-shot molding process. Although this process significantly reduces the cost of manufacture, in the past it has developed a shutoff void designated by the reference numeral 34 in FIG. 2. Particularly in the case of the narrow suture 27, use of the clip 10 can result in the suture 27 falling into the shutoff void 34. This will typically render the clip 10 useless in holding the suture 27 between the jaws 21 and 23.

Figure 3:
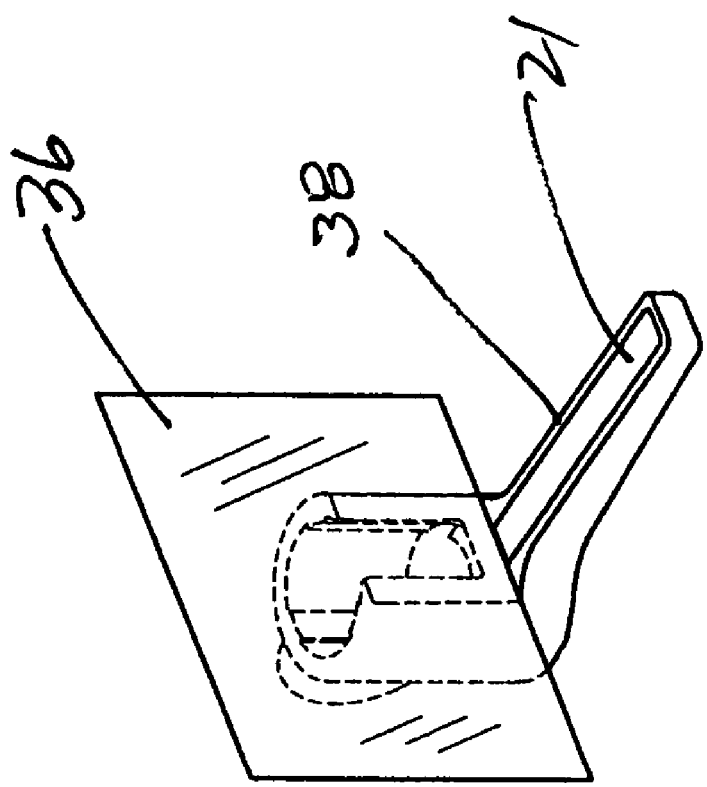
FIG. 3 is a molding step associated with the clip of FIG. 1.

In the past, the shutoff void 34 has developed in the two-step molding process which is discussed with reference to FIGS. 3 and 4. In such a process, the jaw 21 is formed in a first mold, which for purposes of clarity, is not shown in FIG. 3. The plastic forming the jaw 30 is initially heated to a flowable state. In this state, it is injected into the mold and fills the mold cavity which is shaped in the form of the jaw 21 and component 18. In the two-shot molding process, this molded material is left in the mold where it cools and hardens.

A second mold is then formed to receive the softer elastomeric material which forms the pad 30 (FIG. 1). The jaw 21 actually forms part of this second mold which is further defined by a mold shutoff designated by the reference numeral 36 in FIG. 3. This mold shutoff 36 prevents the flowable elastomeric material of the pad 30 from flowing into the component 18 as the pad 30 is formed. With the mold shutoff 36, which helps define the second mold, the pad 30 is formed only on the jaw 21.

Figure 4:
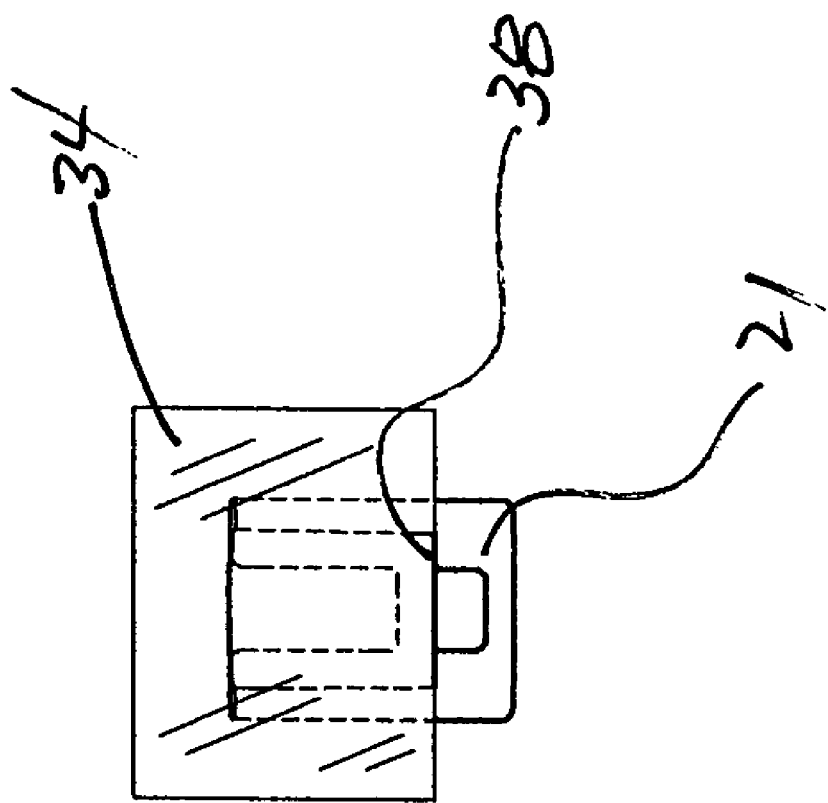
FIG. 4 is a front elevation view of the molding step illustrated in FIG. 3.

As best illustrated in FIG. 4, the mold shutoff 36 in the past has been seated on an upper surface 38 of the jaw 21. It can be appreciated that after the jaw 21 has been molded in a first step and the pad 30 has been molded in a second step, the mold shutoff 36 can be removed and the jaw 21 with pad 30 can be ejected in its final form. In the past, removal of the mold shutoff 36 has left the shutoff void 34 which extends between the pad 30 and the component 18 down to the top surface 38 of the jaw 21. It is this shutoff void 34 which has been particularly problematical in these clips of the prior art.

Figure 8:
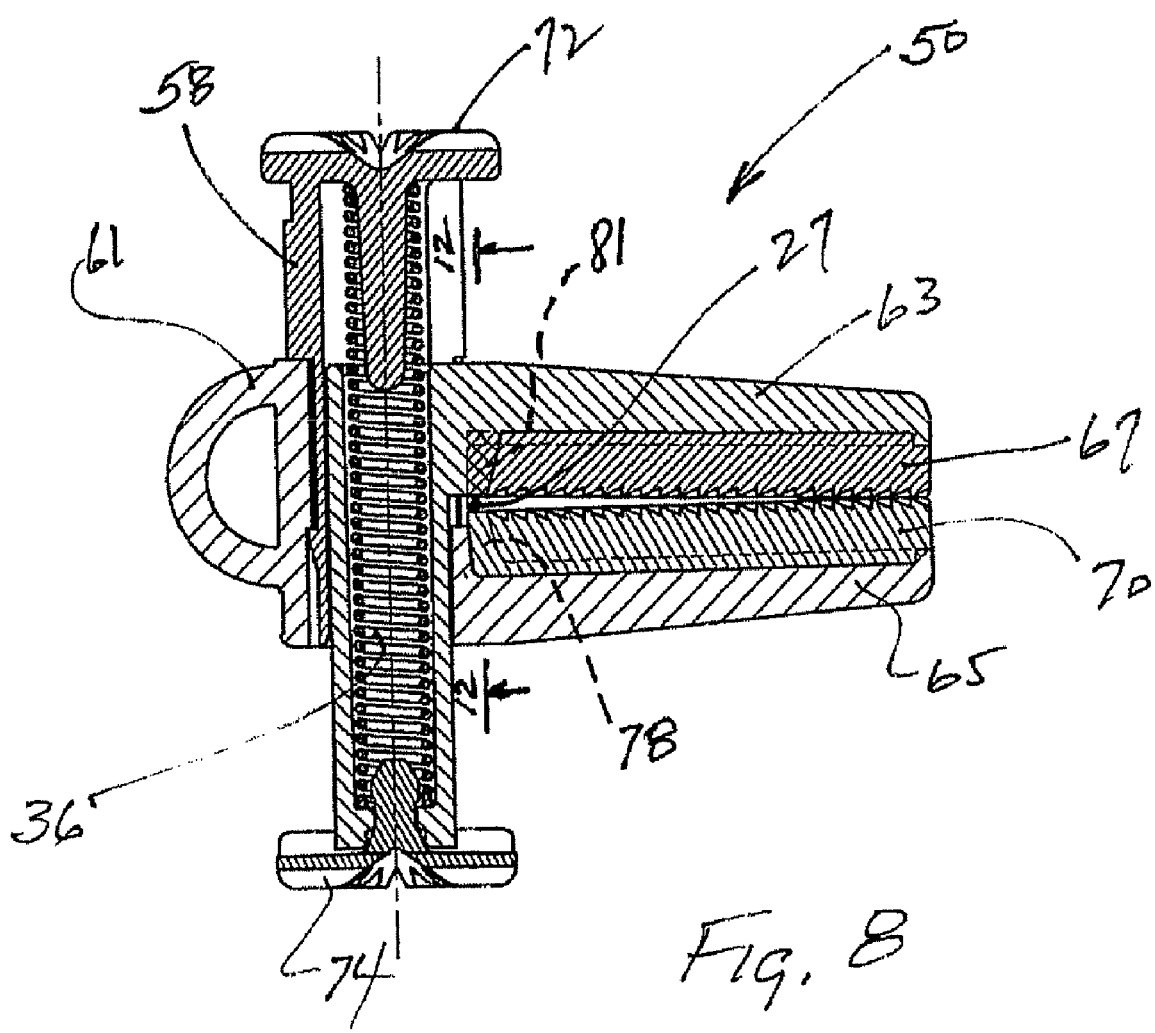
FIG. 8 is a cross section view similar to FIG. 7 with the clip in a closed state.
Figure 9:
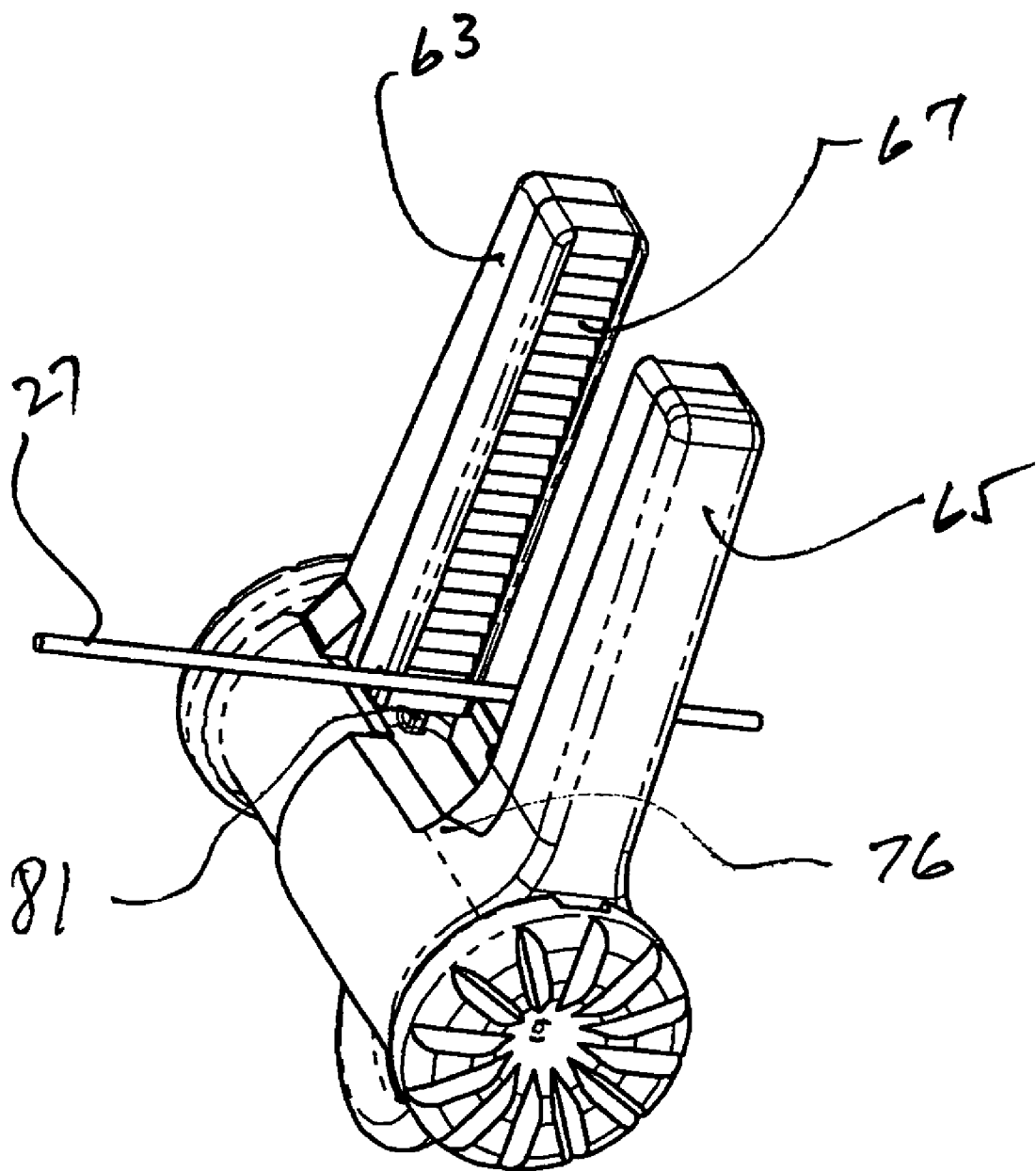
FIG. 9 is a bottom perspective view showing a top rib associated with the present invention.

A surgical clip of the present invention is illustrated in FIGS. 5-14 and designated by the reference numeral 50. The clip 50 includes two telescoping members 52 and 54 which form a housing for a spring 56 best illustrated in FIG. 7. The telescoping member 52 is formed from two parts 58 and 61 for assembly in a snap-fit relationship perhaps as best illustrated in FIG. 8. A first jaws 63 is integral with the part 61 so that it moves in concert with the telescoping member 52. Similarly, an opposing jaw 65 is integral and moves in concert with the telescoping member 54. An elastomeric pad 67 is formed on the jaw 63 while a similar pad 70 is formed on the jaw 65. A finger support 72 can be molded integral with the component 18, while a finger pad 74 will typically be assembled in a snap-fit relationship with the telescoping member 54.

Of particular interest to the clip 50 is a plurality of ribs 76, 78 and 81 which are formed at the proximal ends of the jaws 63 and 65. More specifically, in this embodiment, the ribs 76 and 78 are molded with the jaw 65 while the rib 81 is molded with the jaw 63.

Figure 5:
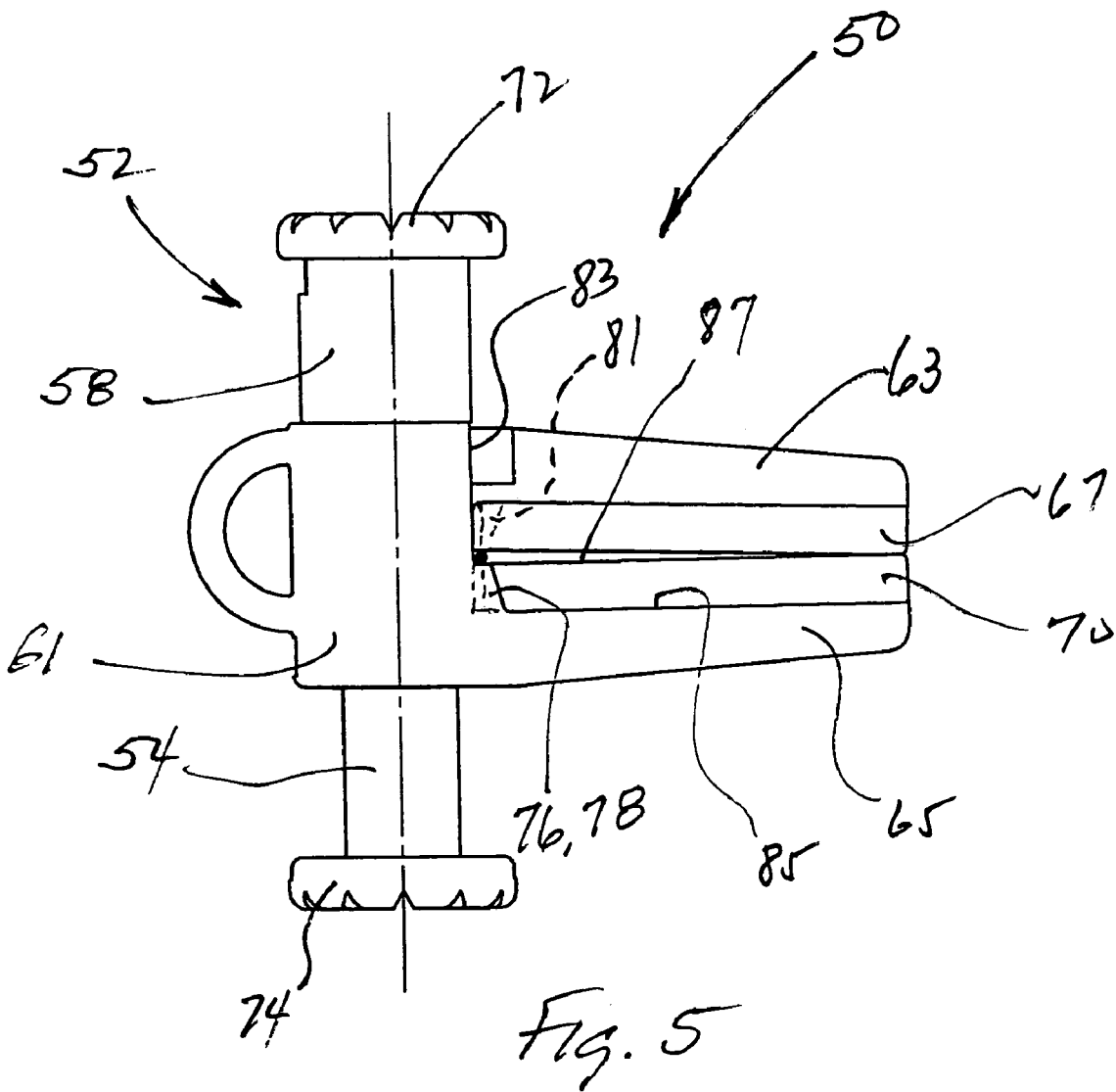
FIG. 5 is a side elevation view of a surgical clip of the present invention.
Figure 6:
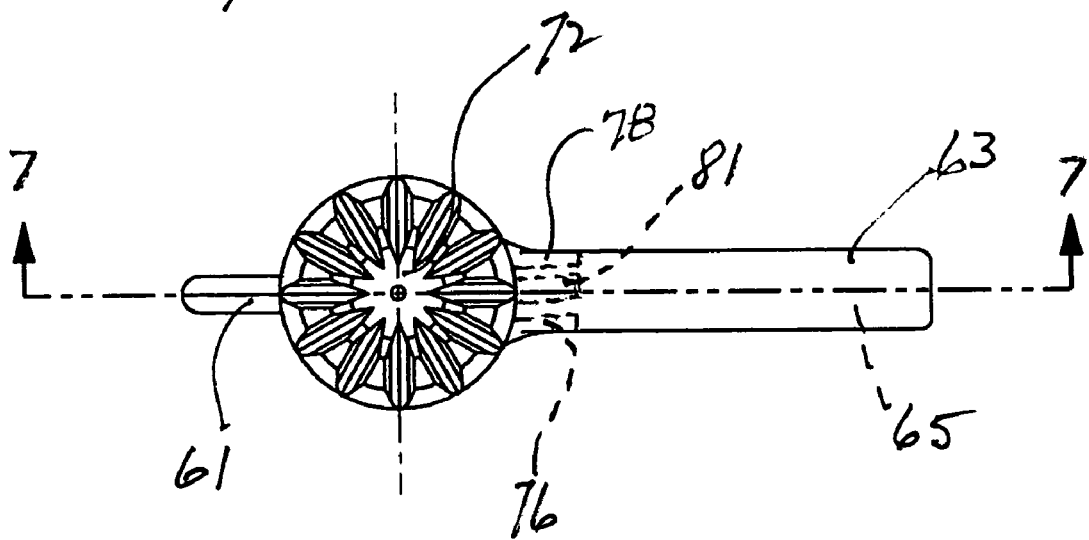
FIG. 6 is a top plan view of the clip illustrated in FIG. 5.
Figure 7:
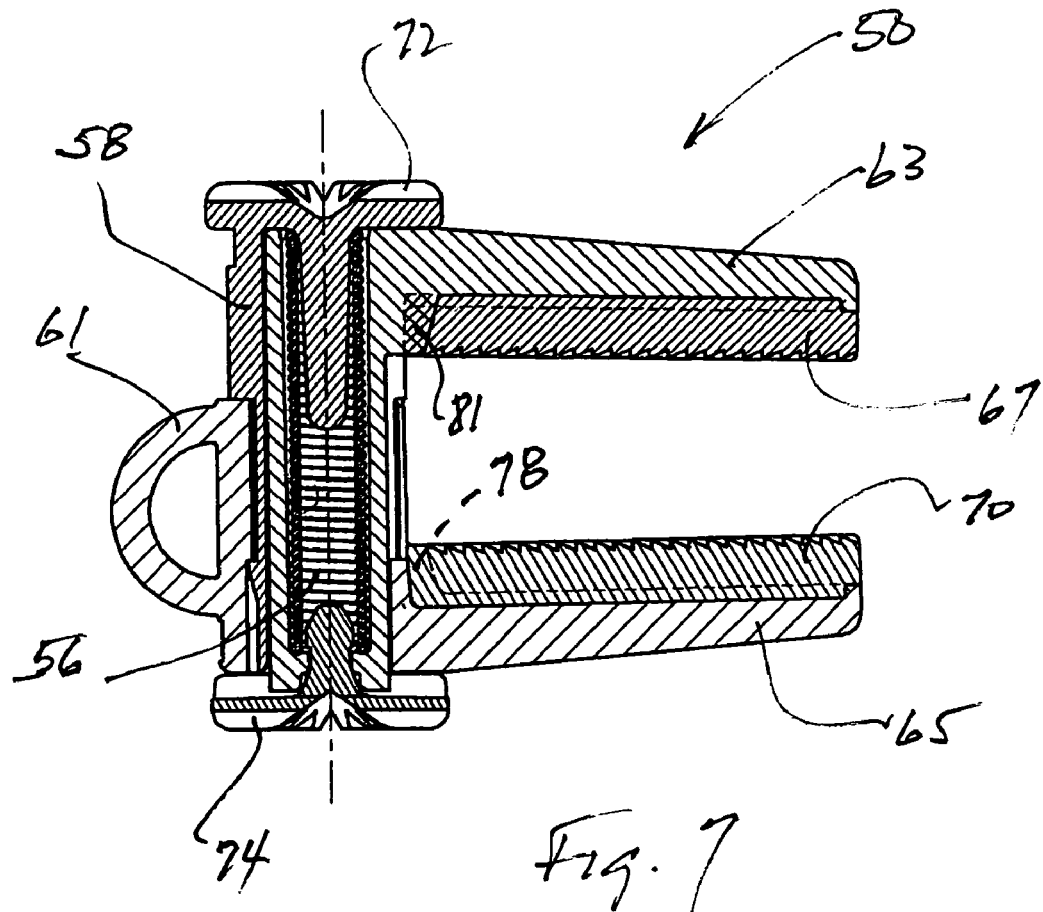
FIG. 7 is a cross section view taken along lines 7-7 of FIG. 6 with the clip in an open state.

The ribs 76 and 78 are molded with the jaw 65 and extend distally from a surface 83 and longitudinally on either side of the jaw 65. In a transverse direction, the rib 76 and 78 in this embodiment extend from a surface 85 of the jaws 65 upwardly in FIG. 5 into proximity with the upwardly facing surface 87 of the pad 70. The rib 81 is similarly formed on the jaw 63, but is positioned laterally between the ribs 76 and 78 as best shown in FIG. 6. This lateral offset ensures that the ribs 76 and 78 do not have an interference fit with the rib 81 when the jaws are in the closed state as illustrated in FIG. 8.

Figure 10:
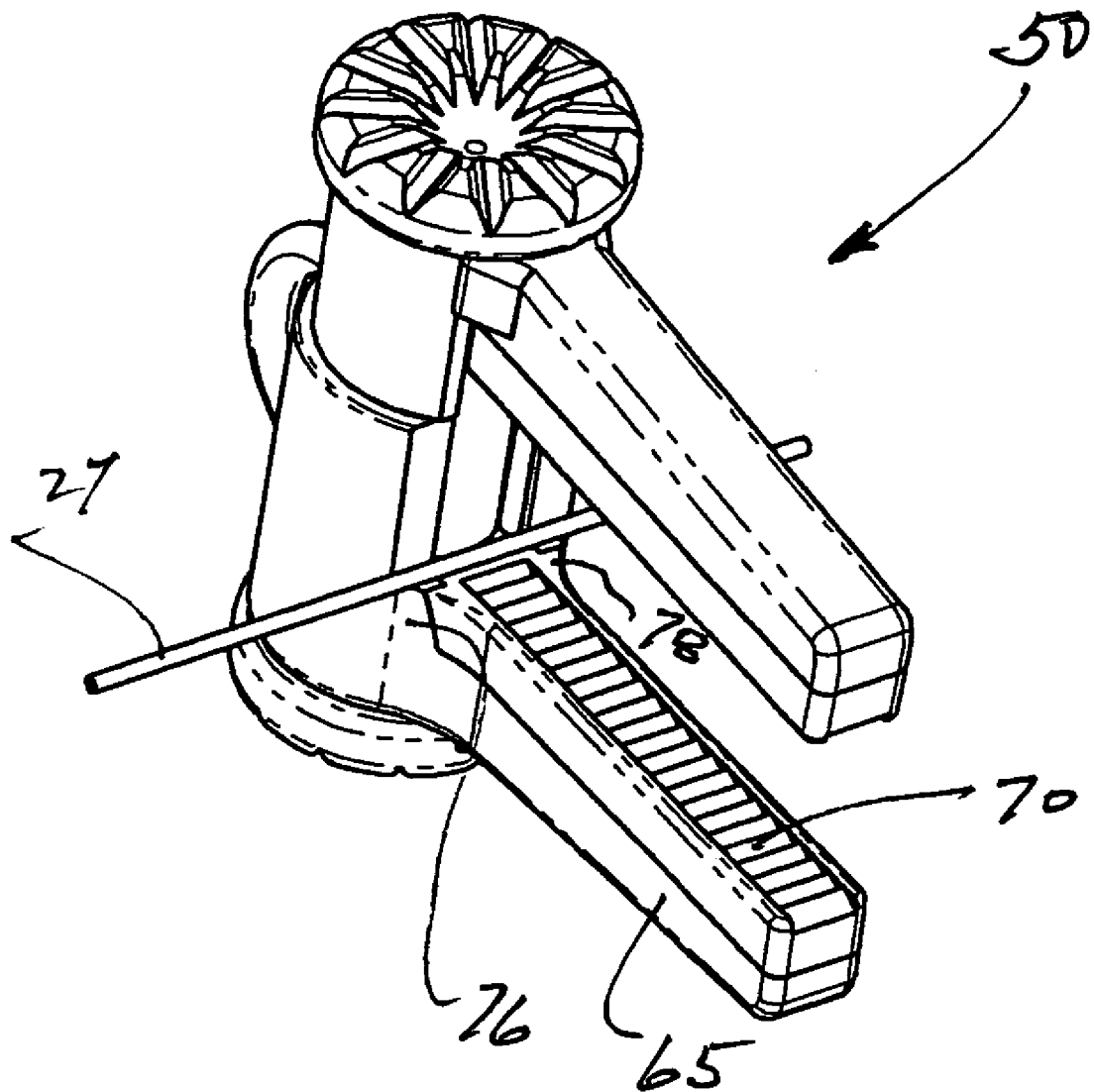
FIG. 10 is a top perspective view showing bottom ribs associated with the present invention.
Figure 11:
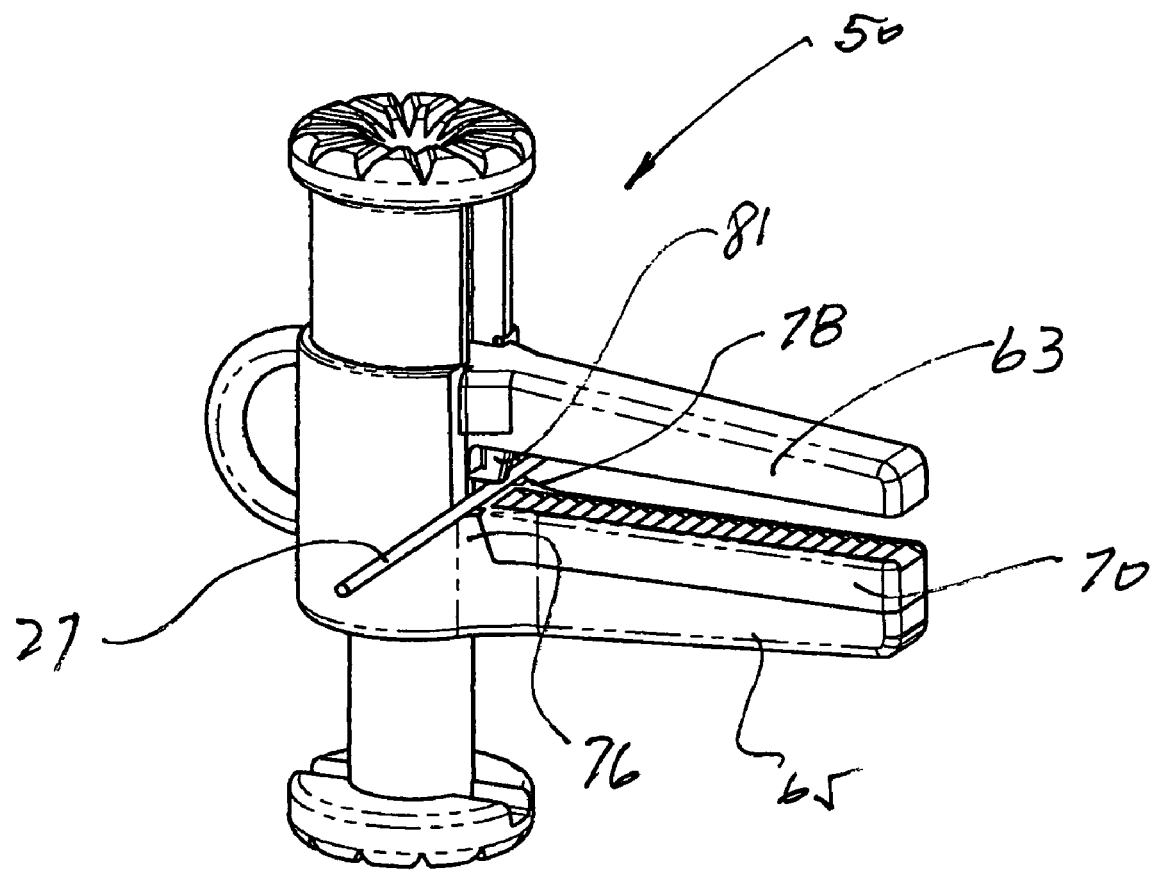
FIG. 11 is a side perspective view illustrating the ribs of the present invention.
Figure 12:
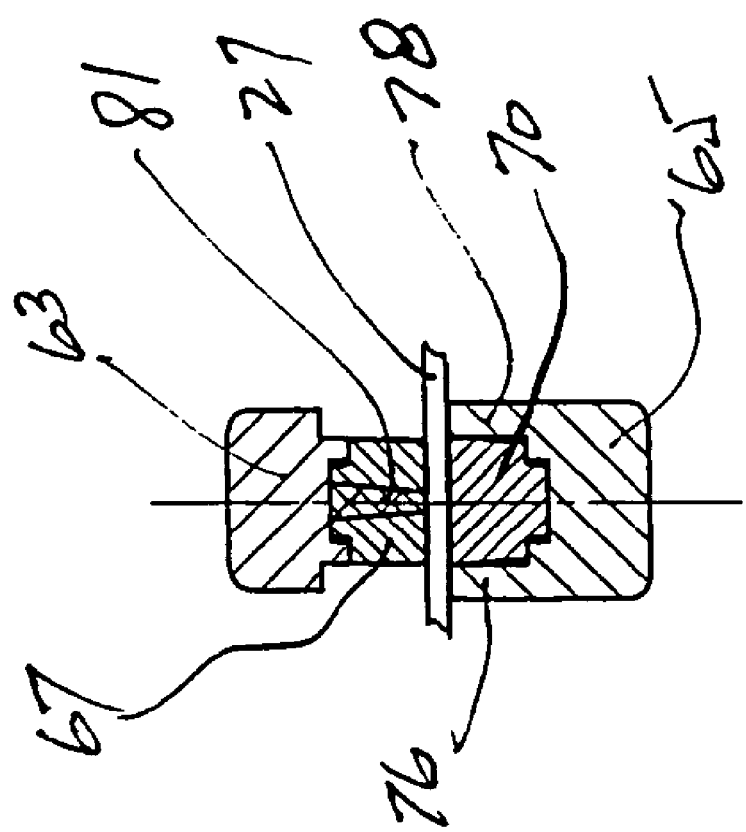
FIG. 12 is a cross section view taken along lines 12-12 of FIG. 8.

It can be seen that with the ribs 76, 78 and 81 formed in proximity to the surface 83, they provide a hard plastic barrier which inhibits the suture 27 from falling into any mold shutoff cavity. Thus, for example, as illustrated in FIG. 5, the suture 27 is held between the soft elastomeric pads 67 and 70 even in proximity to the surface 83. The spaced relationship of the two ribs 76 and 78 associated with the jaw 65 is best illustrated in FIG. 10. As illustrated in FIG. 10, elastomeric pad 67 extends along a planar surface of the jaw 65, and includes a first portion extending distally from each of the ribs 76, 78 and a second portion extending from the outer surface of the housing adjacent to the rib to the first portion of the pad 67. The rib 81 which is disposed centrally of the jaw 63, is best illustrated in FIG. 11 where the associated pad 67 has been removed for clarity. The offset relationship of the rib 76, 78 and 81 is perhaps best illustrated in the cross-sectional view of FIG. 12. Additionally, as illustrated in FIG 12, the second portion of the pad 67 can have a reduced width as it passes adjacent each of the ribs 76,78 as compared to the width of the first portion (illustrated in FIG. 10).

Figure 13:
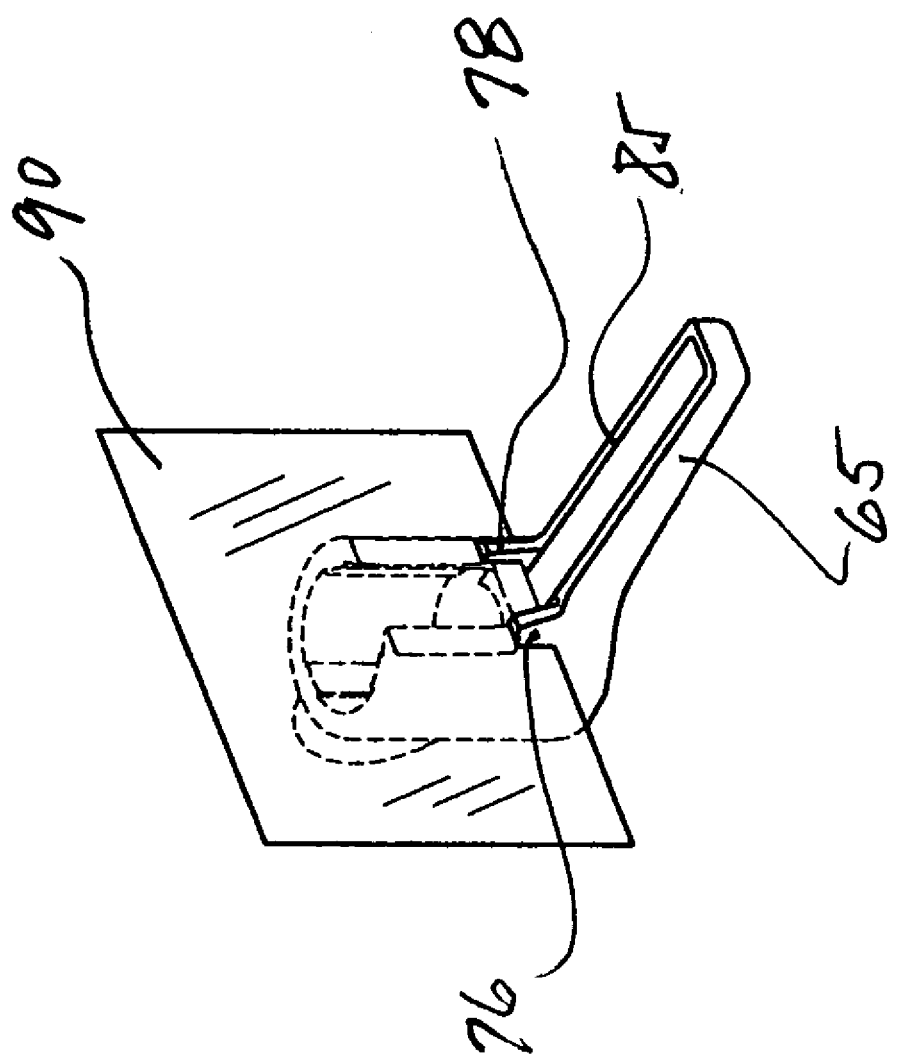
FIG. 13 is a perspective view illustrating a method step in accordance with the present invention.
Figure 14:
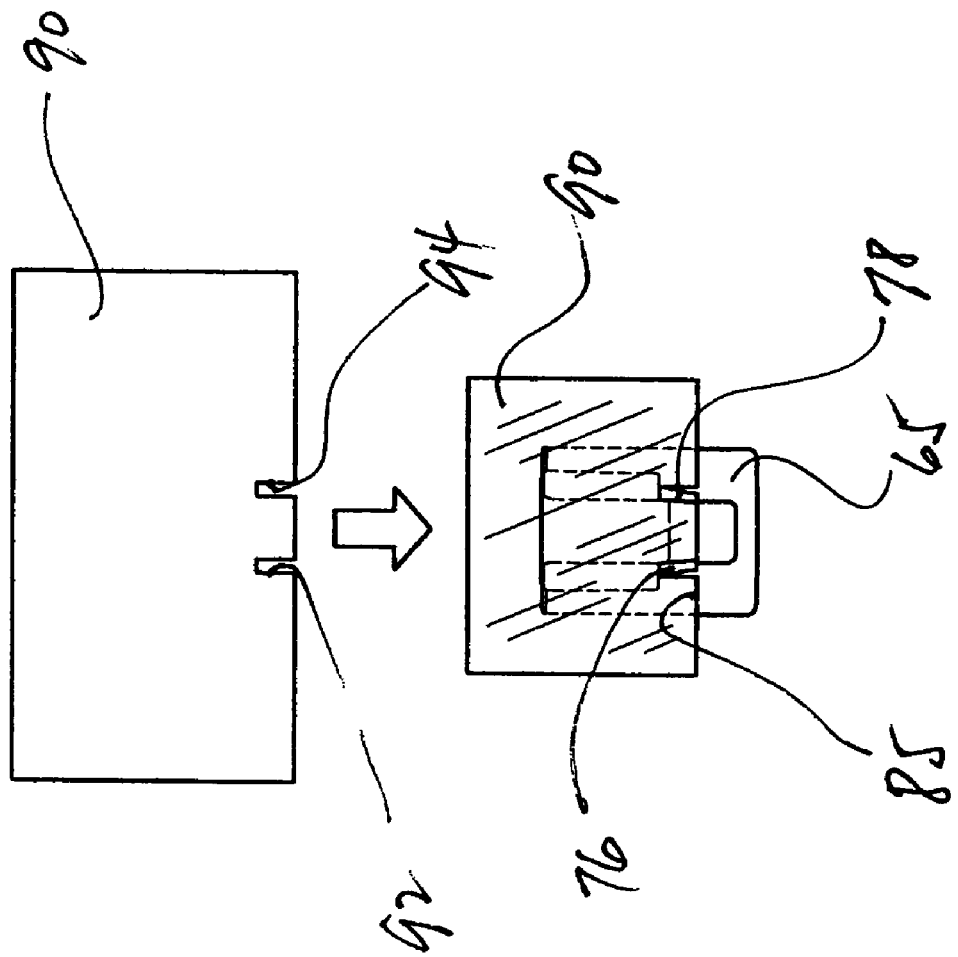
FIG. 14 is a front elevation view of the method step illustrated in FIG. 13.

With the presence of the ribs 76, 78, and 81 in proximity to the surface 83, (FIG. 5), a special mold shutoff 90 must be provided to accommodate the two-step molding process. FIG. 13 illustrates a step in the molding process similar to that discussed with reference to FIG. 3. It will be noted in this case that the mold shutoff 36 is preferably placed against the surface 83 and at least partially seated on the upper surface 85 of the jaw 65. With the presence of the hard plastic ribs 76 and 78 in this area, the mold shutoff 90 must be specially configured so that it can also seat on the ribs 76 and 78. This seating of the mold shutoff 90 on the upper surface 85 and the ribs 76 and 78, is best illustrated in FIG. 14. A more complete understanding of the present invention can be obtained by comparing the method step (FIG. 14) associated with the present invention, with the method step (FIG. 14) associated with the prior art. As best illustrated in FIG. 14, cutouts 92 and 94 must be provided in the mold shutoff 90 to accommodate the ribs 76 and 78, respectively.

Notwithstanding the foregoing distal description, it will be understood that many other modifications can be made to the various disclosed embodiments and method steps, without departing from the spirit and scope of the concept. For example, various sizes of the surgical device are contemplated as well as various types of constructions and materials. It will also be apparent that many modifications can be made to the configuration of parts as well as their interaction. For these reasons, the above description should not be construed as limiting the invention, but should be interpreted as merely exemplary of preferred embodiments. Those skilled in the art will envision other modifications within the scope and spirit of the present invention as defined by the following claims.

The invention claimed is:

1. A surgical clip adapted for use in holding a suture, comprising:
   a housing having an outer surface;
   a first jaw connected to the housing and having a first planar surface extending from the outer surface of the housing along the first jaw, the first jaw having a proximal end proximate the housing and a distal end away from the housing;

a second jaw connected to the housing in an opposing relationship to the first jaw and having a second planar surface facing towards the first planar surface, the second jaw having a proximal end proximate the housing and a distal end away from the housing;

a rib extending out from the second planar surface, proximate the proximal end of the second jaw, towards the first planar surface;

a pad attached to the second planar surface having a first portion extending from the rib distally along the second planar surface and a second portion extending from the outer surface of the housing adjacent to the rib to the first portion of the pad, the second portion of the pad having a width smaller than a width of the first portion of the pad; and a spring disposed in the housing, the spring biasing the first jaw and the second jaw into a closed state.

2. The surgical clip recited in claim 1 wherein the rib is a first rib and further comprising a second rib extending out from the first planar surface towards the second planar surface, the second rib aligned over the second portion of the pad.

3. The surgical clip recited in claim 2 wherein the pad is a first pad and further comprising a second pad attached to the first planar surface extending along the first planar surface and covering over the second rib.

4. The surgical clip recited in claim 1 wherein the rib is a first rib and further comprising a second rib extending out from the second planar surface towards the first planar surface and next to the first rib, the second portion of the pad extending between the first rib and the second rib.

5. The surgical clip recited in claim 4 further comprising a third rib extending out from the first planar surface towards the second planar surface, the third rib aligned over the second portion of the pad.

6. The surgical clip recited in claim 5 wherein the pad is a first pad and further comprising a second pad attached to the first planar surface extending along the first planar surface and covering over the third rib.

7. The surgical clip recited in claim 6 wherein the first pad and second pad abuts the outer surface of the housing.

8. The surgical clip recited in claim 1, wherein the outer surface of the housing and the second portion of the pad define a cavity therebetween, and wherein the rib inhibits passage of the suture into the cavity.

* * * * *